(12) United States Patent
Pabst (10) Patent No.: US 9,488,754 B2
(45) Date of Patent: Nov. 8, 2016

(54) SELF-ACTIVATING ADAPTIVE MONITORING NETWORK AND METHOD FOR REGISTRATION OF WEAK ELECTROMAGNETIC SIGNALS

(71) Applicant: ELWE TECHNIK GMBH, Cremlingen (DE)

(72) Inventor: Michael J. Pabst, Bad Staffelstein (DE)

(73) Assignee: Dipl. oec Knut Thomas Hofheinz, as Liquidator for ELWE Technik GmbH, Braunschweig (DE)

( * ) Notice: Subject to any disclaimer, the term of this patent is extended or adjusted under 35 U.S.C. 154(b) by 304 days.

(21) Appl. No.: 14/384,525

(22) PCT Filed: Dec. 28, 2012

(86) PCT No.: PCT/EP2012/005386
§ 371 (c)(1),
(2) Date: Sep. 11, 2014

(87) PCT Pub. No.: WO2013/097946
PCT Pub. Date: Jul. 4, 2013

(65) Prior Publication Data
US 2015/0052992 A1 Feb. 26, 2015

(30) Foreign Application Priority Data
Dec. 31, 2011 (DE) .................... 10 2011 122 807

(51) Int. Cl.
*G01W 1/16* (2006.01)
*A61N 5/00* (2006.01)
(Continued)

(52) U.S. Cl.
CPC ...... *G01W 1/16* (2013.01); *A61N 5/00* (2013.01); *F03D 11/0033* (2013.01); *F05B 2260/80* (2013.01); *G01R 29/0842* (2013.01)

(58) Field of Classification Search
CPC .................................................. G01W 1/16
USPC ..................................................... 73/170.24
See application file for complete search history.

(56) References Cited

U.S. PATENT DOCUMENTS 5,396,220 A * 3/1995 Markson ................. G01S 3/16
324/72

(Continued)

FOREIGN PATENT DOCUMENTS

DE 19514465 A1 11/1995
DE 19721197 A1 12/1998

(Continued)

OTHER PUBLICATIONS

PCT, Written Opinion of the International Searching Authority, PCT/EP2012/005386, Dec. 31, 2011.*

(Continued)

*Primary Examiner* — David Gray
*Assistant Examiner* — Kevin Butler
(74) *Attorney, Agent, or Firm* — Rankin, Hill & Clark LLP (57) ABSTRACT

In the prior art electromagnetic measurement systems for meteorology are known with which Spherics signals are recorded and analyzed. To design a measurement system in such a way that the creation, development and transfer of discharge processes is relatively observable for comprehensive monitoring network, it is provided, that a subnetwork (SN) is underlain to a base net (BN), wherein in the cells of the subnetwork (SN) sensors (SSN) with the ratio of between 1:8 and 1:12, preferably 1:10, smaller distance are distributed, wherein sensors (SBN) located in the basic network (BN), which are in standby-mode and which if receiving Spherics-burst signals in an adjustable time period are self-activating and make a preprocessing for the extraction of event patterns, and wherein a central station (Z) turns on said sensors (SSN) of the subnetwork (SN) for a finer resolution with respect to the observation.

14 Claims, 4 Drawing Sheets

(51) Int. Cl.
*G01R 29/08* (2006.01)
*F03D 11/00* (2006.01)

(56) References Cited

U.S. PATENT DOCUMENTS

| | | | | |
|---|---|---|---|---|
| 5,541,501 A * | 7/1996 | Shaver | G01W 1/16 | 324/72 |
| 5,545,975 A * | 8/1996 | Youngquist | G01W 1/16 | 324/202 |
| 5,771,020 A * | 6/1998 | Markson | G01R 29/0842 | 324/72 |
| 5,910,765 A * | 6/1999 | Slemon | G01D 1/00 | 340/517 |
| 5,943,629 A * | 8/1999 | Ballard | G01S 19/07 | 702/2 |
| 5,977,762 A * | 11/1999 | Murtha, Jr. | G01W 1/16 | 324/457 |
| 6,012,330 A * | 1/2000 | Palmer | G01W 1/16 | 73/170.24 |
| 6,121,885 A * | 9/2000 | Masone | G08B 17/10 | 340/286.05 |
| 6,122,758 A * | 9/2000 | Johnson | G06F 1/26 | 702/132 |
| 6,164,130 A * | 12/2000 | Pabst | G01W 1/16 | 73/170.24 |
| 6,427,535 B1 * | 8/2002 | Sakai | G01W 1/10 | 73/170.16 |
| 6,552,521 B1 * | 4/2003 | Medelius | G01S 3/808 | 324/72 |
| 6,788,043 B2 * | 9/2004 | Murphy | G01R 29/0842 | 324/122 |
| 6,791,311 B2 * | 9/2004 | Murphy | G01R 29/0842 | 324/72 |
| 6,828,911 B2 * | 12/2004 | Jones | G01W 1/16 | 324/457 |
| 6,984,971 B1 * | 1/2006 | Beasley | G01R 29/12 | 324/457 |
| 7,016,785 B2 * | 3/2006 | Makela | G01W 1/16 | 702/4 |
| 7,049,972 B2 * | 5/2006 | Fabian | G01W 1/16 | 324/72 |
| 7,171,308 B2 * | 1/2007 | Campbell | G01W 1/16 | 702/4 |
| 7,254,484 B2 * | 8/2007 | Jantunen | G01W 1/16 | 702/4 |
| 7,266,455 B2 * | 9/2007 | Kahkoska | G01W 1/16 | 702/182 |
| 7,511,467 B2 * | 3/2009 | Jantunen | G01R 29/0842 | 324/72 |
| 7,515,087 B1 * | 4/2009 | Woodell | G01S 7/22 | 342/175 |
| 7,774,139 B1 * | 8/2010 | Rose | G01W 1/02 | 340/601 |
| 7,809,507 B2 * | 10/2010 | Dwyer | G01W 1/16 | 324/72 |
| 7,868,811 B1 * | 1/2011 | Woodell | G01S 7/22 | 342/175 |
| 7,885,700 B2 * | 2/2011 | Clark | G01R 29/12 | 600/372 |
| 8,010,289 B1 * | 8/2011 | Ryan | G01W 1/16 | 702/176 |
| 8,275,548 B2 * | 9/2012 | Marshall | G01W 1/16 | 324/72 |
| 8,341,106 B1 * | 12/2012 | Scolnicov | G06N 7/005 | 702/50 |
| 8,427,333 B2 * | 4/2013 | Kraemer | G01R 29/0842 | 324/72 |
| 8,890,704 B2 * | 11/2014 | Barrieau | G01R 29/0842 | 324/72 |
| 9,179,531 B2 * | 11/2015 | Melito | H05F 7/00 | |
| 2009/0301224 A1 * | 12/2009 | Sihler | F03D 7/04 | 73/862.333 |
| 2010/0077850 A1 * | 4/2010 | Matsushita | F03D 80/30 | 73/170.24 |
| 2013/0265851 A1 * | 10/2013 | Faber | G01V 1/42 | 367/25 |
| 2014/0347181 A1 * | 11/2014 | Luna | H04M 1/72569 | 340/539.22 |
| 2014/0355380 A1 * | 12/2014 | Barral | G01V 1/3808 | 367/16 |
| 2015/0052992 A1 * | 2/2015 | Pabst | G01W 1/16 | 73/170.24 |
| 2016/0033317 A1 * | 2/2016 | Aharoni | G01D 18/00 | 73/1.16 |

FOREIGN PATENT DOCUMENTS

| | | |
|---|---|---|
| DE | 102004000024 A1 | 10/2005 |
| DE | 102004000025 A1 | 3/2006 |
| EP | 0990177 B1 | 1/2003 |
| EP | 1355165 A2 | 10/2003 |

OTHER PUBLICATIONS

Cummins L., Kenneth, Lightning Detection Methods and Meteorological Application, Global Atmospherics, Inc., Sep. 2000, pp. 1-13.*

* cited by examiner

SELF-ACTIVATING ADAPTIVE MONITORING NETWORK AND METHOD FOR REGISTRATION OF WEAK ELECTROMAGNETIC SIGNALS

The invention relates to a measuring network for registration of weak electromagnetic signals and to a method for this purpose.

Spherics is of short duration, often consisting only of a few vibrations of damped, vertically and horizontally polarized vibrations which arise by charge displacements or charge movements in the troposphere. The frequencies are between 3 and 100 kHz, the amplitudes at up to 1000 times of normal radio transmission, the pulse repetition frequency is a maximum of 150 Hz and the typical pulse duration is between 35-250 µs. Main sources of Spherics are storm whose lightning activities generate electromagnetic fields, as well as air electrical fluctuations which are caused by the movement and friction of large air masses. Since it is often the causative lightning is dark-field discharges not visible (without thunder), this Spherics, i.e., the pulse-like appearance of electromagnetic waves of natural origin within the Earth's atmosphere, is often referred to as dark lightning.

The activities of Spherics will be used in meteorology for weather forecast, whereby with their help digital weather data gained in the weather stations forecasts can be significantly be enhanced. For the data transmission to a central station usually cable-based transmission path or transmission via analog, ISDN or radio modems is used. In modern weather stations message transmission paths based on the Internet Protocol are increasingly used, whereby weather data via standardized protocols are available in local area networks (local area network LAN) and wireless networks (wireless local area network WLAN), but also worldwide via the Internet or via SMS.

From DE 10 2004 000 024 A1 a system and a method for detecting, transmitting and analyzing of data and information incurred by electromagnetic radiation is known, in which the sensitivity for detecting the electromagnetic radiation is as high as possible and simultaneously detects as few spurious signals. For this purpose, the system comprises:
 several measuring stations,
 at least one particular broadband antenna body for detecting said signals assignable to electromagnetic radiation signals,
 with at least one station electronics remotely located from the antenna body for processing the acquired means of the respective antenna body signals to the data and information and
 with at least one memory unit for storing the processed data and information of the station electronics and
 at least one central station to which at least a part, in particular at least one selected parameter, of the data from the respective measuring station, acquired processed and stored information can be transmitted,
 at least one self-regulatory threshold by which the sensitivity of the station electronics, in particular at least one filter unit of the electronic station depending on the occurring noise, especially from the random noise level, can be set, in particular optimized, is.

More specifically, the electronic station comprises
 at least one amplifier unit for low-noise amplifying the signals detected by the respective antenna body,
 at least one filter unit for filtering the signals amplified by the amplifier unit, in particular with regard to, for example, radio stations which originating technical noise, and
 at least one analog/digital converter unit for converting into digital output signals the by means of the filter unit filtered signals.

Further, at least a frame buffer is provided which is connected to the signals, in particular with the digital outputs of the analogue/digital converter unit, and which is designed if relevant for the caching of these signals, in particular this output signals. By means of a read-out unit for continuous retrieval of passing through the block buffer and/or necessary latched signals is allowable. Furthermore, a signal analyzing means is connected downstream to the read-out unit for analyzing and/or for processing of the data read out from the readout unit and output signals from the block buffer and further in particular for continuously determining the noise level. Finally, a threshold determination unit for determining at least one optimum threshold value in function of the determined noise level and a signal analysis unit for applying the self-regulatory threshold with this determined optimal threshold is provided. The measuring stations are arranged at a distance of about one hundred kilometers one another and are respectively in two-way, and in particular wired and/or wireless communication with the central station. The antenna body is designed to mechanically self-supporting shape without moving and/or weather-sensitive components for outdoor use, whereas the primary circuit of the antenna body is electrically isolated from the secondary circuit of the antenna body and the electromagnetic fields are broad-band and low-noise decoupled and thus time true measurable. The central station comprises at least one evaluation means by which the information provided by the respective stations data and information, especially at high rates and/or in particular without loss of time, can be evaluated, and further comprises at least one warning unit for outputting graded and/or fully automatic warnings before climatological and/or meteorological processes, especially of thunderstorms. The reported data and information based on historical, in particular obtained by means of long-term measurement data and information are determinable by means of Model Output Statistics. Finally, at least an interface in particular assigned to the central station is provided to include at least one other climatological and/or is a meteorological data and source of information for the characterization of the overall weather situation in particular by means of Model Output Statistics. The system according to DE 10 2004 000 024 A1 enables detection of weak real signals, because the threshold is automatically adjusted depending on the existing noise to the lowest possible value. The self-regulating signal threshold, which can be independent functional and/or technically from dead time of the detection and/or from the parallel processing circuit, this is usually only active during too high data attack. The self-adjusting threshold grants the adaptive finding out of the noise limit, which is difficult, according to statistical noise effects caused for example by the differences between day and night transition and/or weather effects. The features and functions of the central that can be associated with up to a hundred sensors consist, inter alia:
 in the signal storage,
 in the implementation of a method for locating discharge sources, such as lightning, for climatological and/or meteorological purposes involving extremely weak signals from weak atmospheric discharge (silent discharge <-> flash-like event) to optimize early detection of thunderstorm cells,
 in the implementation of modules for on-line processing of large data/information rates, wherein a package of data and information, which is disassembled into individual packets over fifteen seconds (timestamp) arrives; a logical ring structure goes to an evaluation unit implemented in the central processing unit (→ Software for Central Station for the detection and evaluation of lightning), whereby a bearing and evaluation based on a time-Sort according to concentration is done (optimized number of five to six sensors), in carrying out a method for detecting of signal ranges for early detection of storm cells, in carrying out a method for analyzing of types of signals, or of groups of data and information for characterizing of meteorological classes and consequently to create flash cards, in the implementation of a method for dynamic spatial extrapolation of storm tracks identified storm cluster and in a module for fully automated and stepped storm warning in the form of text, warnings and sending them to the user by means of a transmitter unit.

In a development of this, according to DE 10 2004 000 025 A1, an accurate characterization of the pulse source, such as a reliable discrimination between cloud-to-ground lightning (cloud-ground) and cloud-to-cloud lightning (intra-cloud) within a cloud or between clouds (cloud-cloud) is allowable. For this purpose, the system for detecting, transmitting and evaluating by means of, in particular low-frequency electromagnetic radiation generated data and information, comprises a plurality of spatially separate stations each comprising at least a particular wide-band antenna body for detecting the electromagnetic radiation attributable to signals and with at least one time-measuring device, in particular at least a global positioning system clock for determining the respective time profile, in particular of the respective time of arrival of the detected signals. The electromagnetic radiation is derived from at least one pulse source of natural and/or non-natural origin, in particular of at least an atmospheric discharge and from at least one transmitter. Here, the height of the pulse source, in particular the emissions level and the transmission level and/or the directionality, particularly the spatial direction of the course, the pulse caused by the pulse source or pulse output transmission is locatable. For this purpose, the deviation of the arrival time of the signal of the pulse source nearest to the measurement station to the arrival time of the signal to at least one, preferably at least two, of the same pulse source, not the nearest stations is determinable. In particular in linear shaped pulse sources, the directionality of the pulse delivery or a pulse transmission is substantially vertical identifiable, if the amplitude of the signal is proportional reciprocal to the distance of the pulse source of the relevant station. This is identified as substantially horizontal if the amplitude of the signal is different from the reciprocal proportionality, said deviation by taking into account the angle of elevation and the angle between the discharge pulse and pulse transmission axis, in particular discharge axis, and direction to the station is correctable. Furthermore, several signals originating from a spatially and/or temporally limited range of pulse sources can be combinable to groups. The deviation of the amplitude of a single signal can be placed in relation in particularly to the mean deviation of the amplitude of the signal of the associated group, and in particular to eliminate a variable ground conductivity caused by damping effect. If pulse output or pulse transmission is from heights area in kilometers by comparing the measured distributions of time deviations of at least two pulse delivery or pulse transmission times, in particular at least two discharge times, of the nearest measurement station and of the at least two of the same pulse source, not the nearest stations, is detectable. The height of the pulse source and/or the directionality of the pulse delivery or pulse transmission is determined by means of the measurement station nearest to the pulse source and by means of a single pulse of the source that is not the nearest station, if the direction of incidence of the pulse delivery, or pulse transmission can be determined. In the system according to DE 10 2004 000 025 A1 the bearing does not occur with only one or two of the pulse source nearby, especially near lightning, sensors in a direct way, i.e. not by site-level targeting with the height, but through the use of deviations of the signal arrival times at each of the pulse source nearest, especially lightning next sensor stations over others, the pulse source not nearest, especially not lightning next sensor stations. Here, in the network control center by means of special algorithms, in particular by means of algorithmic pattern recognition, it was found from the numerous incoming signals from the individual sensors, those which belong to the same pulse event. For this purpose, the data received from the various sensors single peak patterns are "overlaid" in digitized form in order to can identify in this way the initial peak clearly. By means of this "matching" method a time-accurate and therefore good DF result is achievable, which in turn is essential for the bearing to the heights. This allows achieving the high sensitivity event and the thus resulting high number of primarily detectable signals can actually continue to be used and can useful exploited also in terms of signal properties. To account for the origin of the discharges the network according to DE 10 2004 000 025 A1 is extended to a three-dimensional mode (so-called 3-D mode) so that emission levels of pulses, especially of discharge, could be determined. Such an approach offers a number of technical and economic advantages:

because only one station must be nearest to the pulse source, especially in lightning, large sensor distances are possible, i.e. not a dense expensive network is required;

due to the use of Global Positioning System-controlled time measurement even larger distances of up to about one hundred kilometers to the lightning-station "close to the pulse source" may be considered as "lightning near" and significant, i.e. for the bearing to the heights usable time deviations can be produced;

the use of very low frequency measurement networks (=range to tens of kilohertz) ensures a wide range of the pulse source, not the nearest stations, for example, the flash stations not flash next (which must capture the flash also), i.e. established VLF networks can be used if the time measurements are accurate in microsecond range;

the system as well as the procedure can be based on the hardware of conventional 2D lightning detection method; a use of "real" 3D techniques to radio or VHF range is not necessary if the goal of the present invention is not the precise spatial resolution of discharge channels, for example, from lightning channels in the 100 meter area, but to provide a data base for a decision on the question is whether the detected event is to be classified as intra-cloud pulse;

the existence of pulse delivery or impulse transmissions, especially of lightning emissions from kilometer heights can be recognized theory-free and without the assumption of adjustable parameters by a comparison of at individual (each lightning next) sensors and at groups of (not blitz next) sensors measured distributions of time deviations of two pulse delivery times (determined by bearing in the whole of the net pulse time minus difference of arrival time and duration of each pulse of the source nearest station), in particular two flash times (determined by bearing in the whole of the net flash time minus difference of arrival time and duration of each flash next station);

emissions levels can be calculated by algorithms which are at least comparable to those of the bearing in local by adding the height variables;

the method can be integrated in other existing pulse positioning systems, especially lightning detection systems, if the necessary time accuracy provided is achieved;

the method can also be applied to low intensity pulses, especially if low-intensity flashes are used, provided that the pulse, especially the flash, is measured at three sensors, when using incident directions for taking bearings also only measured at two sensors;

the results of the method can be used to clarify ask to a pulse shape discrimination of cloud-to-cloud discharges (IC), in particular of cloud-to-cloud lightning, against cloud-to-ground discharges (CG), in particular cloud-to-ground flashes and the system as well, the method may be used together with the pulse shape analysis for discriminating, to solve the (small) proportion of disputed cases, which is clearly not determinable by a method or by other methods.

Furthermore EP 1 355 165 A2 discloses a method and apparatus for earthquake and volcanic eruption prediction and for sorting of the epicenter by Sferics-Technics-Spectrum analysis. To provide a Sferics-Technics-Spectrum analysis which does not require a low-frequency signal receiver as narrow coils and for this purpose suitable amplifier and analyzers atmospheric, low ELF-/VLF signals (ELF Extremely Low frequency, VLF Very Low Frequency) or electromagnetic fields in the form of Sferics, atmospherics, Technics are detected by antenna elements, the ELF-/VLF-signals or the electromagnetic fields are (real-time) filtered, (real-time) spectrally analyzed for determining the extended time, most low-frequency ULF anomalies (envelope/surrounding), and from this the origin, especially the direction of the ULF anomaly is located by means of several receiver-/analyzing unit arranged by a large distance, especially at a distance of more than a thousand kilometers. The reported ELF-/VLF signals or electromagnetic field signals are sectorally decomposed to origin or direction of locating of the ULF-anomaly in their direction components and analyzed in this form. The apparatus is characterized by a plurality of one another electrically and/or electromagnetically connected Sferics-Technics or weather radiation detection units and associated signal processing units.

at least two on earth remotely placed Sferics-Technics AC signal detection systems, each with at least three antenna elements, which are aligned in each vertical or vertical, horizontal predominantly east-west and north-south direction and the detection systems downstream connected satellite data processing, ELF-/VLF-acquisition and ULF-study units. Linked via the feed elements the antenna elements have a length of at least a few decimeters and are made of an electrically and electromagnetically conductive material. The Sferics-AC-signal amplifier in the detection systems comprises broadband a frequency range of a few tens of kilohertz frequency upper limit to less than/equal to a few Hz and has a signal dynamic range of 50 dB. In particular, the bodies responsible for collecting horizontal Sferics-Technics activities, vertically arranged antennas with associated antenna signals and subsequent Sferics-Technics signal analysis on a number of directional sectors to less than/equal to 90 degrees are divided. Here, the antenna direction sectors having in the directions North, South, West, East, a characteristic lobe to the smaller/equal to +/−45 degrees. In particular low frequency high magnetic conductive, so having a high permeability metal elements provided—preferably MU MetaII—to the Sferics-Technics signal antenna element is V-shaped, an angle less than/equal to 90 degrees inclusive, are formed. Finally, the V-shaped direction selection antennas are manually and/or motor-controlled pivoting or rotatable positioned.

EP 0 990 177 B1 of the Applicant discloses an electromagnetic measurement system for meteorology, wherein the Spherics signals are recorded and analyzed. In this measuring system, from the consideration is started that the one of a plurality of measuring stations disposed distributed spatially in the form of a measurement station net in a predetermined spatial area, provides a better indication of the general weather patterns by an analysis of the change of a Spherics signal which this influenced in the atmosphere through along its propagation. In particular, through an extensive, continuously taking place measurement of Spherics signals in addition to the current one weather phenomena also their causes, such as air movement and discharge processes could be recorded, so that with regard to the future development of a particular weather forecasts for short-term (typically 15 minutes to 2 hours), high accuracy is possible. Basic idea of this measuring system of the applicant, therefore, is to set up an electromagnetic measurement system for meteorology, whose stations are represented by stochastic events occurring naturally within the atmosphere, and its receiver through a network of stations are formed. Moreover, this measurement system is based on the consideration that the Spherics signals along its propagation path in the atmosphere influenced by locally different thermodynamic and electrical conditions, and by this way addition conclusion about the current weather conditions and resulting conclusions about a prediction could be derived. The data thus provided by this measurement system, giving a comprehensive picture of the weak atmospheric VLF-emissions. This data can be used not only as a basis for a reliable short-term weather forecasting, but also as a reliable basis for the epidemiological investigation of biotropic effects of VLF pulses on the human organism. The average distance between adjacent stations, i.e., the mesh size of the grid monitoring network, is preferably between 10 and 50 kilometers, especially about 30 km. This enables a good coverage of Spherics activities with a resolution of about 10 km. In a preferred embodiment of the measuring system, each station is provided with a processing unit for deriving data from the Spherics signals received. The processing unit may have simple analog filters and/or signal processing modules, by which the analog signals are processed, so that measuring channel information are present in analog form. In particular the processing unit comprises a digital signal processor, an analog-to-digital converter is connected upstream. In this case, the Spherics signals are subjected to a digital signal analysis, for example an additional digital filtering, in particular a spectral analysis or time-series analysis of successive Spherics signals. Derived from the signal processor by means of such an analysis measurement data are then transmitted as a digital data word to the central evaluating unit.

Finally, from DE 195 14 465 A1 of the applicant, a simpler, faster and more accurate analyzer for Spherics signals is known, comprising a signal input and a processing and treatment device for incoming Spherics signals and a result signal output, wherein the processing and conditioning means contains a fuzzy-logic-unit which is adapted for evaluation of the fuzzy Spherics signals. The fuzzy-logic-unit takes into account for the evaluation of the Spherics signals unsharp signal criteria, such as the rate of rise, the initial amplitude, the wave number, the frequency distribution, the amplitude distribution and/or the decay of the oscillations of the signals and pulse repetition rate, and the frequency distribution of the frequency values occurring. For each criterion, the membership functions are determined for fuzzification, and the fuzzy-logic-unit contains a fuzzy-logic-circuit for defuzzification. Further, the fuzzy-logic-unit is adapted to obtain a decision on the basis of the assessment of the received signal, whether it is a Spherics signal or interference, and/or if the signal is derived from the near or far field. For this purpose, the processing and processing means comprises a fuzzy logic unit upstream to analog to digital converter and one storage means for storing input signals upstream to the fuzzy-logic-unit. Signals stored in the memory means are sequentially read-out for processing and editing by the fuzzy-logic-unit from the storage device and available to the fuzzy-logic-unit. Further for receiving Spherics signals, a signal input is provided which is connected upstream of the antenna arrangement which is a direction-selective and/or sensitive to magnetic field variations, and which includes an active antenna with an antenna body having a pre-amplifier and an impedance transformer. Furthermore, between the antenna array and the signal input is arranged an amplifier and filter means comprising a filter unit of SC filters and which restricts the receiving area of the analyzer between 3 kHz and 60 kHz. Preferably, the fuzzy logic unit consists of a two-part logic circuit, wherein the first part of the circuit serves as a signal identifier based on a predefinable parameter, and the second part of the circuit is adapted to perform a combination of the parameters with each other so that the respective signals, in particular to be detectable clear as Spherics signals and disorders are separable. In this case, pulse widths of up to a few 100 microseconds, vibrational frequencies between 3 kHz and 100 kHz, in particular between 3 kHz and 60 kHz, pulse repetition rates between zero kHz and 150 Hz and the maximum signal amplitude in the range of several mV/m to a few V/m are measured and evaluated.

The present invention is a monitoring network and a method for registering a weak electromagnetic signals (discharge channel in the region of $10^1$ and $10^2$ m, the current in the range of $10^1$ amperes), which are referred to as Spherics-burst, and arise in particular in convection cells and which are clearly different to typical lightning (discharge channel $10^3$ m, discharge current $10^3$ amps). Through a reliable detection of these Spherics-bursts (dark lightning and thunder barely audible) the local prediction as to the likelihood of imminent occurrence of lightning/lightning strikes could be substantially improved.

The mechanism of this weak Spherics-burst signals can be explained as follows: charge clusters that already occur in early development stages of a convective cell can discharge burst like, with the resulting pulse shapes and frequency components, by connecting through so-called "hydrometeors" (ice needles that are align in an electric field and a filament form).

It is an object of the invention, compared with the known measuring systems and methods for meteorology, to improve it in such a way that the creation, development and transfer of discharge processes are relatively observable for comprehensive monitoring network.

This problem is solved, in the case of a measuring network for registration of weak electromagnetic signals comprising a base network with a plurality of measuring stations, which are distributed spatially in a predetermined spatial region, and each having an antenna and at least one sensor for receiving the electromagnetic signals, and a transmission unit for transmitting from each measuring station to an evaluation unit arranged in a control center present measurement data, derived from the electromagnetic signals, and, wherein the distance between each adjacent measuring station of the basic network is between 10 km and 50 km, according to the invention, wherein a subnetwork is subordinated to the base network, wherein sensors) are distributed in cells of the subnetwork in a smaller distance with a ratio of between 1:8 and 1:12, preferably 1:10, wherein sensors located in the basic network, which are in standby mode and which if receiving Spherics-burst signals in an adjustable time period are self-activating and make a preprocessing for the extraction of event patterns, and wherein the central station turns on said sensors of the subnetwork for a finer resolution with respect to the observation.

Furthermore, the problem is solved, by a method for registering weak electromagnetic signals in a measurement system comprising a base network having sensors and a subnet with sensors subordinated to the base network, wherein
 if receiving Spherics-burst signals incoming in an adjustable time period, the mode sensors of the basic network that are in standby-mode are self-activating,
 a pre-processing for creating event patterns is performed by the sensors of the basic network and
 for finer resolution with respect to the observation the center turns on the sensors of the subnet.

The measurement network and as well the method according to the invention does not aim as in the prior art, in particular in DE 10 2004 000 024 A1, DE 10 2004 000 025 A1 and EP 1355165 A2, the "bearing" of "lightning" as they occur within clouds, between these or between clouds and earth, but on the observation of these weak discharge processes, i.e. the Spherics-burst signals, which typically take place within a cloud. Therefore, the registration devices (sensors) can be equipped with relatively simple antennas that consist of mutually orthogonal ferrite rods (alternatively, these could also be represented by simple Helmholtz coils). Through the combination according to the invention, namely "expensive measuring equipment/small number of measurement points" and "simple measuring instruments/high number of measurement points", in a surprisingly simple manner, a significant improvement is achieved in comparison to known observation methods. The processing of the received signals within the central office does not happen from the standpoint of physical analysis of each individual signal itself, but from the point and purpose to put together from the "delivered" event patterns of the sensors a "discharge Weather-map", which then in conjunction with other meteorological parameters should be interpreted. Thus, the measurement network and as well the method according to the invention could be used in projects, which are intended to improve the weather warning. In particular, in a nationwide extremely close-meshed network (mesh size <=1 km) with significantly simplified measuring instruments for pressure, humidity, temperature, precipitation and wind speed.

In a preferred embodiment of the invention, the sensors of the base network makes a preprocessing of the Spherics-burst signals in such a way, that the received signal after an A/D-conversion are lead over digital band-pass filter working in parallel and the pulse signals located at the ends of the respective frequency bands are in each case analyzed by downstream connected digital signal processors in accordance with frequency of the pulses and power density.

This embodiment of the invention has the advantages that by the smart sensors of the basic network and thus recovered and transferred to the transmission unit for forwarding to the central, the evaluation unit, which is arranged in the central, can perform the evaluation of "event patterns" cheaper, simpler and faster.

Further advantages and details can be found from the following description of a preferred embodiment of the invention with reference to the drawing. In the drawings shows.

Figure 2:
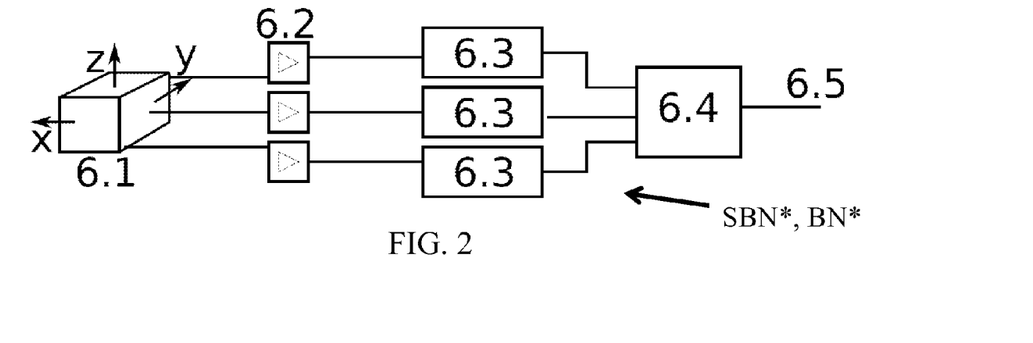
FIG. 2 an embodiment of a basic network in the prior art.

The monitoring network and method according to the invention for registration of weak electromagnetic signals comes from an electromagnetic measurement system for meteorology according to EP 0 990 177 B1 of the applicant with a basic network BN* having a plurality of stations that is shown in FIG. 2. The stations/sensors SBN* for receiving the electromagnetic signals are spatially distributed in a given space region, and each have an antenna orthogonal 6.1 for x, y, z—the coordinate space in each channel (XYZ), an input preamplifier 6.2, one that downstream arranged evaluation unit 6.3 and a transmission unit 6.4 connected to this unit 6.3 for communicating each present at the measuring stations/sensors SBN* and from the electromagnetic signals derived measurement data to an evaluation unit assigned to the stations/sensors SBN* and arranged in a central Z. The distance between each adjacent stations of the basic network BN* is between 10 and 50 kilometers.

Figure 1:
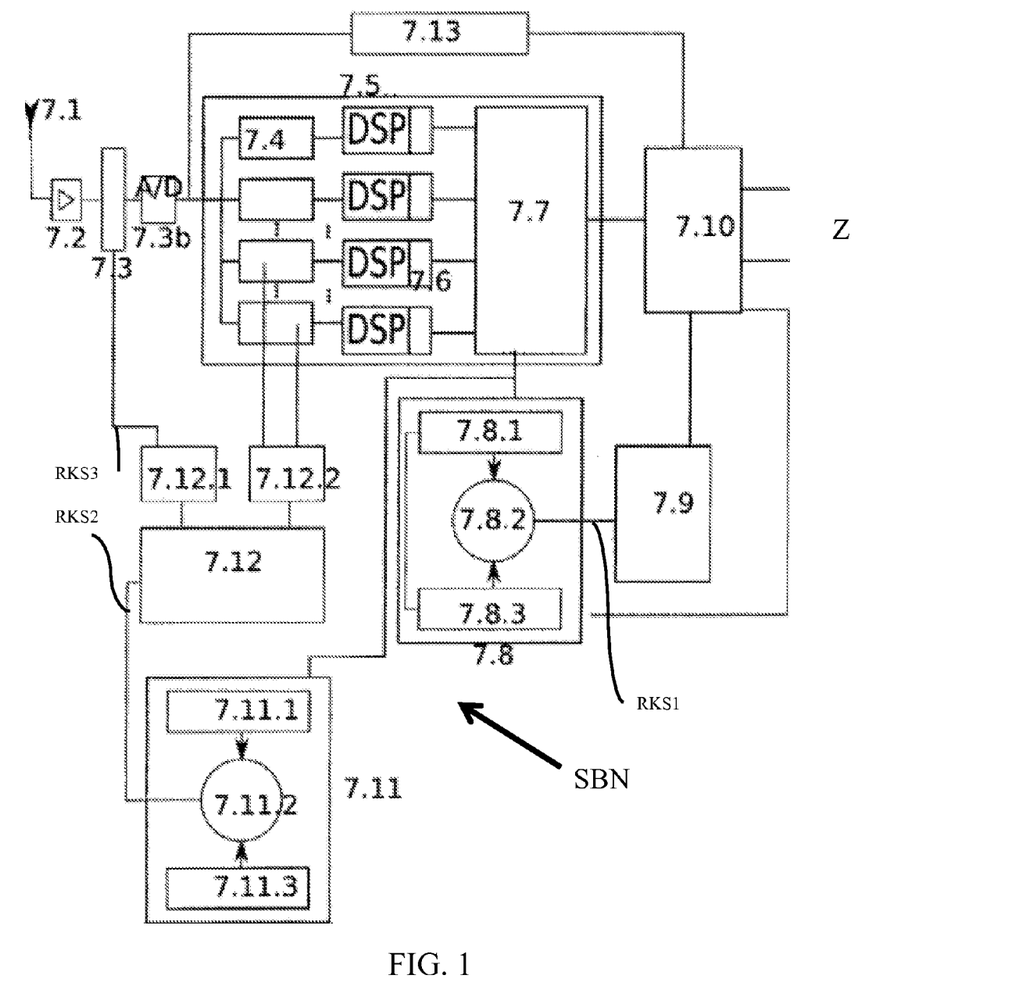
FIG. 1 a preferred embodiment of the sensors SBN of the basic network BN.
Figure 8:
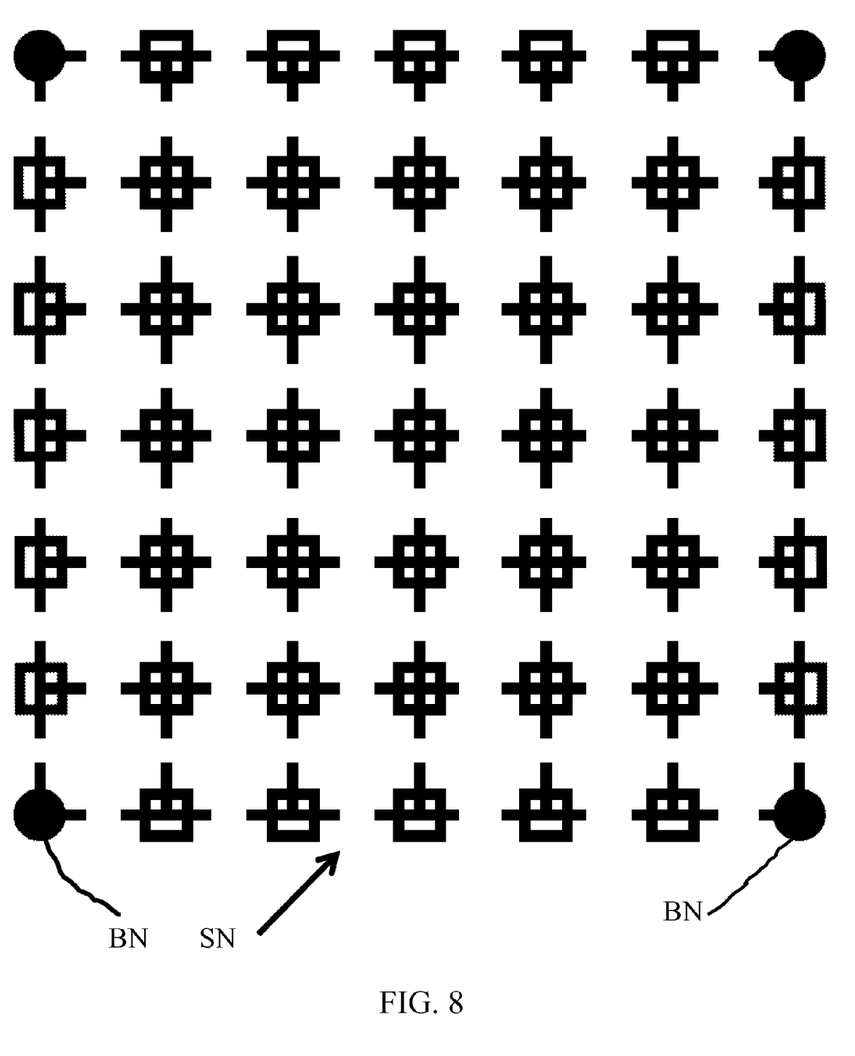

The self-activating and adaptive measurement network according to the invention is a subnet SN underlain to the base network BN (see FIG. 8), wherein in the cells of the subnet SN sensors SSN with a ratio between 1:8 and 1:12, preferably 1:10, smaller distance are distributed. The sensors SBN of the basic network BN are in standby mode, one embodiment is shown in FIG. 1, which if receiving Spherics-burst signals in an adjustable time period are self-activating and make a preprocessing for the extraction of event patterns and according to these patterns—according to the invention—the central Z for finer resolution with respect to the observation switches on that sensors SSN of the subnet SN.

Furthermore, in the self-activating and adaptive monitoring network the sensors SBN have three feedback loops, namely a self-activation RKS1, one for the addition of further frequency bands R S2 in the sensor SBN and one to lower the threshold value RKS3 in the input circuit of the sensor SBN.

Specifically, the sensors SBN of the basic network BN take a preprocessing of the Spherics-burst signals in such a way, that the received signal after an A/D-conversion 7.3.$b$ is passed through parallel-operating digital band-pass filter 7.4 and the signals located in the respective frequency band are analyzed according to the pulse rate (number of times per time) and power density (amplitude) in all three spatial coordinates X, Y and Z by means of digital signal processors DSP 7.5, 7.6 each connected downstream. With the digital signal processors DSP 7.5, 7.6 an evaluating unit 7.7, for example a single-chip computer with associated memory unit working as evaluating unit 7.7, is connected for generating an event pattern. At the output of said evaluating unit 7.7 for self-activating of the sensor SBN of the base network BN a modular comparator 7.8 is arranged, wherein in the first module 7.8.1 of said modular comparator 7.8 the event sample at time $T_1$ is stored, wherein in the third module 7.8.3 a so-called default pattern is impressed and wherein the second module 7.8.2—in the case of identity of two successive event patterns stored in the first module 7.8.1 and the third module 7.8.3—delivers a signal to a power supply unit 7.9 determined for a transfer unit 10.7 and activates them. The in the third module 7.8.3 deposited event pattern is either impressed to the sensor SBN, for example, in a ROM, or in the case, that the transmission unit 7.10 is active, be amended by the central Z forth. Comparator 7.8.2 is either a "Holistic" Comparator according to the teaching of DE 197 21 197 A1, that is, a processing means for processing an input data structure containing a mapping means for mapping the input data structure in a multi-dimensional analog image data structure with an analog memory means for storing the analog image data structure, and a comparator for comparing the analog image data structure with at least one analog reference data structure and mapping the comparison result in an output data structure, are performed in a miniaturized form, or there is a regular bit pattern using an example single-chip computer. The transmission unit 7.10 can be executed in the context of the invention as a programmable "Open-Platform Mobile" using conventional mobile networks. Thus the signals supplied by the evaluation 7.7 or a recording unit 7:13 (for details see below) are transmitted to the central Z or they received form the central Z a changed "default" pattern. The power supply of the switchable power supply unit 7.9 itself can be done via the local network or via solar panel with battery backup.

For the addition of further frequency bands and for the variation of the input sensitivity in the sensor SBN of the basic network BN is arranged a comparator 7.1 1 comprising a two-memory 7.1 1.1, 7.1 1.3 that is connected to the evaluation unit 7.) and to a switching unit 12 having a plurality of switches 7.12.1, 7.12.2. If the event patterns stored in the first memory 7.1 1.1 at the time Tn+1 are different from the event patterns stored in the second memory 7.1 1.2 at time Tn, the comparator 7.11 by means of a switch 7.12.2 gradually added on frequency bands by means of a switch 7.12.1 or lowers the threshold in a gate circuit 7.3 to be connected with the antenna 7.1. A switching unit (switch) 7.12 preferably cyclically switched added stepwise frequency bands by the switching functions in 7.12.2 for evaluating particular higher frequent frequency components (to the VHF-range) of the received signal and via the switching unit (SW) 7.12.1 for lowering the threshold in the gate 7.3. As soon as the event sample no longer change in the memories 7.1 1.1 and 7.1 1.3, and thus no difference signal is generated, this process is terminated.

Further, the antenna 7.1 of the sensors SBN of the basic network BN is connected with a input preamplifier 7.2 and this preamplifier 7.2 to the gate circuit 7.3 for an adjustable threshold value, wherein to the gate 7.3 a plurality of digital band-pass filter 7.4 (in the embodiment shown in FIG. 1 four band-pass filter) with a bandwidth of preferably between 10 kHz and 20 kHz are connected and that according to the invention band filter 7.4 (in the embodiment shown in FIG. 1 six band filter) serve as the default setting for processing the frequency components of the signal, preferably between zero kHz and 150 kHz (as a predominant frequency components at Spherics-burst signals) and other digital band-pass filter 7.4 can be switched on gradually. Thus an extension is possible up in the VHF range.

For the registration of the real time signal, the sensors SBN of the basic network BN comprise a recording unit 7.13, which is configured as a single-chip computer with the corresponding flash memory and is programmable so that the recorded time is set either fixed (for example, between 2 and 5 minutes) or can be changed from the central Z via a return channel.

Figure 3:
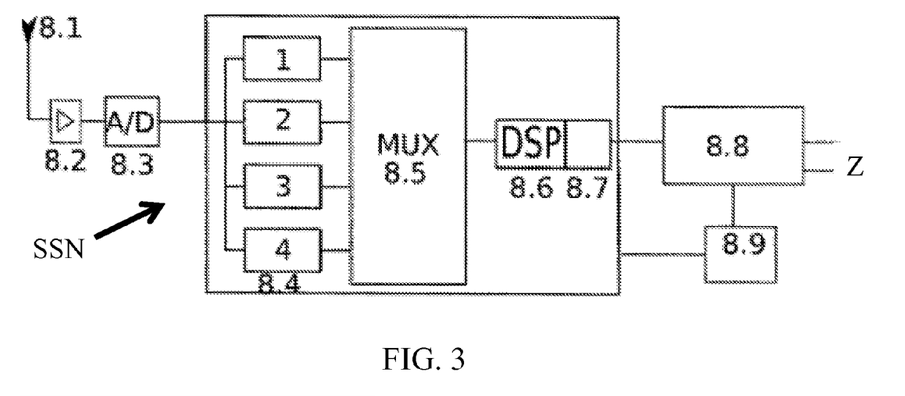
FIG. 3 a preferred embodiment of the sensors SSN of the subnet SN.

The SSN sensors of the subnet SN shown in FIG. 3 do not have feedback loops. In detail, the SSN sensors of the subnet SN have an input preamplifier 8.2 connected to an antenna 8.1, at the output of the preamplifier 8.2 an A/D converter 8.3 is connected. At the output of the A/D converter 8.3 a plurality of digital band-pass filter 8.4 operating in parallel is connected (in the embodiment shown in FIG. 3, four) to the outputs of which are connected a multiplexer 8.5 for common control of a digital signal processor DSP 8.6 and a downstream evaluation unit 8.7. At the output of the evaluation 8.7 a transmission device 8.8 is connected. In standby-mode only the transmission device 8.8 of the sensors SSN of the subnet SN is powered from a power supply 8.9. For finer resolution with respect to the observation, the power supply 8.9 is switched on from the center Z via a return channel for the aforementioned modules of said sensors SSN.

The inventive method for registration of Spherics-burst signals is characterized in that if receiving Spherics-burst signals incoming in an adjustable time period, the mode sensors SBN of the basic network BN that are in standby-mode are self-activating, that a pre-processing for creating event patterns is performed by the sensors SBN of the basic network BN and that for finer resolution with respect to the observation the center Z turns on the sensors SSN of the subnet SN. The sensors SBN of the basic network BN will only be activated and a transfer of the information to the control center Z is only triggered if at least two event patterns arriving during the period which correspond to a specified, gained through past observations. In the context of the invention the event pattern stored in the sensors SBN of the basic network BN can be changed by remote control, when showing during the operation that a change of the event pattern elected at the first start-up of the sensors SBN of the basic network BN according to lightning frequency and/or topography seems to make sense.

The novel self-activating and adaptive monitoring network is summing up characterized in that
(1) the number of measuring stations SBN, SSN is increased substantially, and in the previous mesh size of 30×30 km, the subnet SN is written with a mesh size of less than or equal to 5 km (dependent on the topography), which is equipped with simpler stations SSN.
(2) the measuring stations SBN are in a standby-mode and are only through observed discharge processes/Spherics-burst signals self-activated. Standby-mode means that the overall functionality of a sensor SBN is only activated and transmitting the information to the central Z only be triggered if sequentially in a defined, adjustable period of at least two event patterns arrive, which match a given, gained through past observations. This event patterns can be changed in the measuring station SBN remotely if shown during operation that a change of the selected "default" pattern appears to make sense. This may include functionalities such as these are described in EP 0 990 177 B1 of the applicant.
(3) the measuring stations SBN themselves behave adaptively (or can be adapted by remote maintenance) by, for example, the station SBN automatically
(3.1.) added frequency bands so long further to the selected in the default setting frequency bands (by activating the associated band-pass filters in the input) until the found signals therein do not exceed a defined threshold,
(3.2.) increases the input sensitivity as long (i.e., the threshold for the signals in nano-tesla is lowered so long) by remaining unchanged in frequency bands, until the thus observed signals cannot be separated from the "noise".
(4) the monitoring network remains furthermore insofar as adaptive, that the measuring stations SBN of the basic network BN (see (1)) in the presence of a particular event pattern, activate both the measuring stations SSN in the subnet SN, as well as other stations SBN of the basic network BN.

This achieves two things:

A much finer resolution with respect to the observation, e.g. convective cells in the clouds with respect to their origin location and their extent.

A discriminator function, such as when two or three adjacent stations SSN of the subnet SN differ (appropriately selected high input sensitivity) in their observation. Technical interferers, such as demolition sparks of electrical machines and the like, though have certain similarities in terms of the frequency spectrum with the atmosphere generated by discharge processes signals, but are in their field strength and within their reach so low that they cannot be received by all stations SSN of the subnet SN. Conversely, this means that, if all stations SSN of the subnet SN register a signal, this can be attributed with high probability on atmospheric discharge processes.

The novel self-activating and adaptive measuring network/method/monitoring network is also adaptive to both the mesh size and the number of stations used, as also in the characteristics of the measuring stations itself.

Figures 4, 5:
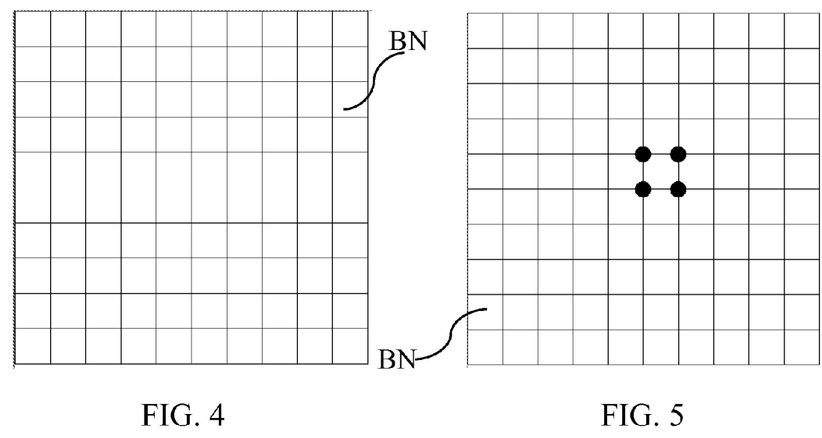
FIG. 4 a schematic representation of the base network BN inactive.
FIG. 5 the active base system BN according to FIG. 4 with four self-activated sensors SBN FIG. 6 the active base system BN according to FIG. 5 with further eight other self-activated sensors SBN, FIG. 7 the active base system BN according to FIG. 4 with a total of twenty-four self-activated sensors SBN and FIG. 8 a schematic representation of the active base network BN of FIG. 5 and a to the basic network BN subordinated subnet SN with SSN sensors according to the invention.
Figure 6:
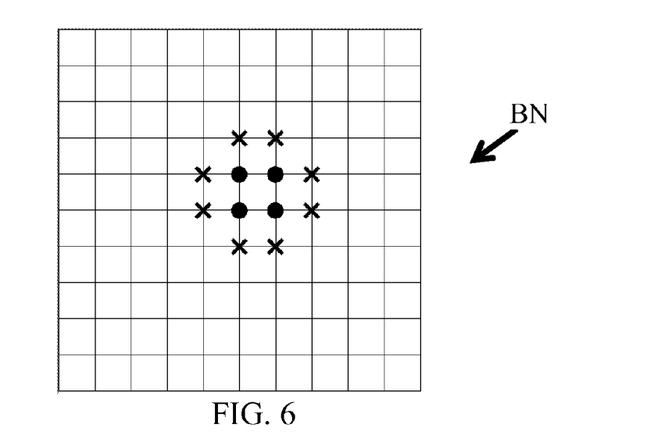
Figure 7:
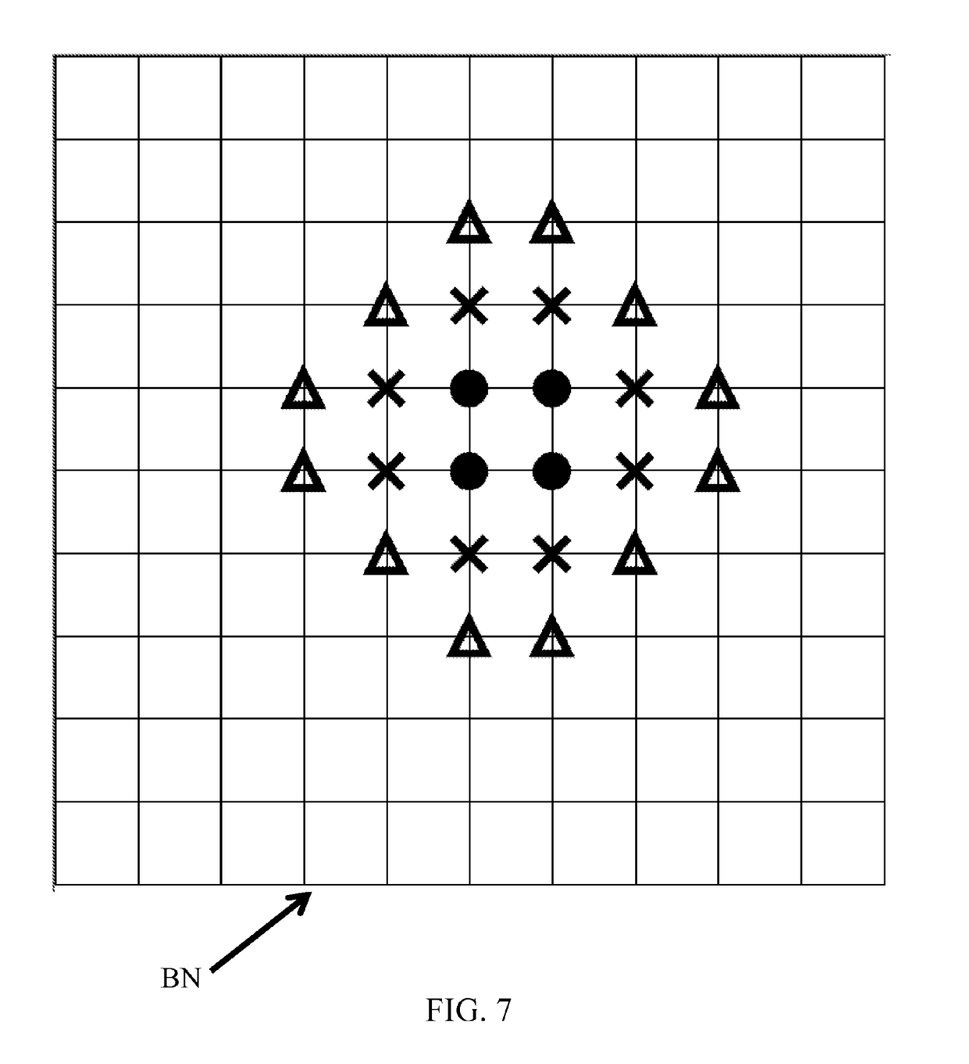

The FIG. 4 shows a schematic representation of the inactive base network BN with a mesh size of for example 30 km. Illustrated in FIG. 5 is the active basic network BN according to FIG. 4 with four self-activated sensors SBN (see the four points); shown in FIG. 6, the active base system BN includes further eight self-activated sensors SBN (see the eight crosses). Furthermore, in FIG. 7, the active base system BN represented with a total of twenty-four self-activated sensors SBN assumed here that in the outer region take place no more discharge activities and self-directed extension process ends. The FIG. 8 finally shows a schematic representation of the active base network BN of FIG. 5 with a subnet SN with sensors SSN subordinated to the base network BN, which—according to the invention—being activated from the control center Z as soon as it detects that a detailed analysis of the processes is necessary.

According to the invention the monitoring network is both self-activating and self-deactivating designed. The deactivation process is to be understood as an inverse function of the activation process. While the activation after the arrival of at least two recognized as relevant event patterns takes place, there is the automatic deactivation when within a set time period, no new signals are registered at the respective sensor SBN of the basic network BN. In this case, the following sequence occurs:

With occurrence of the first events the sensors SBN of the basic network BN are activated and—as already described—the neighboring stations are automatically added. The thunderstorm cell moves across the entire monitoring network, and while the first activated sensors SBN of the basic network BN are already disabled again, another new sensor SBN along the pulling direction of a thunderstorm cell is activated if necessary. After completion of the weather event the entire network goes back to stand-by mode. Using the monitoring network according to the invention spatially and temporally very precise the emergence and further development of a storm can be predicted. This opens up for the lightning protection new perspectives, as by the evaluation in the control center Z of the monitoring network storm can be accurately predicted, and even before the appearance of lightning strikes to the customer (e.g. operators of wholesale or sporting events, airports and air traffic control, horticulturists and farmers, utilities and wind power operators and others) can introduce protective or preventive measures. At the first appearance of atmospheric discharges within an area it can be tested in which the direction this emerging thunderstorm cell will develop. In exceeding the agreed probability of a thunderstorm with the customer in the customer's area will be given the first warning to him. The warning message itself is always agreed exactly with the customer and is based on existing messaging systems, for example by e-mail, fax, SMS-message to a cell phone, phone call, remote data transmission or through the Internet. This is of particular importance in the field of aviation meteorology (air traffic control can alert the pilot in time enough of the impending danger and this can fly around the obstacle or after a backup round lands belatedly but surely) or in the field of industrial safety of data processing center (those data processing centers operate usually with a USV-system (and more rarely with a power system)) or antenna masts and radio equipment in exposed places (these systems can be taken in the short term during a thunderstorm risk completely out of order, so the risk of damage can be drastically reduced) or in the area of sports or recreational outdoor events where the organizers are notified of the fact informed that a thunderstorm in the suit is. Furthermore, from the weather data (similar to the network load control for power supply companies, in which a control variable for the expected power consumption within the next 30 to 90 minutes is determined and transferred to the EVU, so that the energy flow optimized and the over- or under-supply with electrical energy can be reduced) and an additional control variable for controlling the heating and/or air conditioning can be derived, which greatly on days with varying solar radiation (cloudiness change) helps to smooth the control process of heating and/or air conditioning and thus saving energy in the range between 5% (building with pure heating technology in a convenient location) up to about 15% (building with full air-conditioning in an unfavorable position).

The properties described here of the monitoring network, namely event-driven close-meshed increasing the network at the same time of an increasing number of observables by frequency bands and power density classes, allows gaining new insights into the biotropic effects of Spherics and Spherics-similar VLF signals.

In the literature, there are numerous publications in which from significant up to highly significant correlations of Spherics and Spherics-similar VLF signals with certain diseases (such as juvenile epileptics or the increase of myocardial infarction) and/or physiological changes are described. It was found in the recording of brain waves, that there was a so-called remanence—the changes decreases not abruptly, but slowly after exposure to Spherics signals. The problem with all these studies is that the respective test groups were relatively small, the follow-up periods were relatively short, and the investigations were each very restricted. To date, no "receptor" could be found, over which the Spherics and Spherics-similar VLF signals are "coupled" in biological systems. All published studies are therefore qualitative reports and no quantified investigation within the meaning of an experiment, which must be repeated with the same boundary conditions on all places at all times with identical results.

With the measured power according to the invention, it is possible over an area, such as the size of the Federal Republic of Germany to make records over a very long period of time and to compare these records with disease events and progression of the disease to an extremely high number of patients. Thus, for the first time an as certain proved statistical basis could be created, the analysis of this basis contributes to explain the causal sequence of interaction between Spherics and Spherics-similar loan VLF signals and biological systems. This also applies to tectonic events and their relationship with Spherics and Spherics-similar VLF signals. In the literature, there are numerous indications that tectonic shifts that precede an earthquake, for example, is also mapped in Spherics and Spherics-similar VLF signals. In this case, these signals occur independently of, for example, the development of convective clouds that precedes a thunderstorm. As a cause "disturbances" in the eddy currents of magma are presumed caused by relative displacements of individual layers to each other. In consequence, this means that a measuring network, which during the observation becomes always close meshed and more and more parameters be detected, whose operation due to the selected properties is costly, and an improvement in the field of earthquake prediction and volcanic eruption prediction is caused.

The invention is not limited to the described procedure or function blocks, but also includes other procedures that will have the same effect essential to the invention. Thus, in the context of the invention, depending on the topography (e.g., Northern Germany with miles of wide flat terrain) instead of an evaluation for the x, y, z-spatial coordinates (polarization of the source signal and estimation of the altitude of the sensors to the source signal) an examination only in XY-direction could be done or it does not have the same number of sensors SSN of the subnet SN are kept in each cell of the basic network BN. Furthermore, the invention has so far not yet defined in combinations of features, but can also be defined by any other combination of specific features of all the individual features disclosed. This means that any individual feature can be omitted or replaced by at least an individual feature disclosed elsewhere in the application.

The invention claimed is:

1. A measuring network for registering weak electromagnetic signals used to make an observation comprising a base network with a plurality of measuring stations, which are distributed spatially in a predetermined spatial region, and each having an antenna and at least one sensor for receiving the electromagnetic signals, and a transmission unit for transmitting present measurement data from each measuring station to an evaluation unit arranged in a control center, said present measurement data being derived from the electromagnetic signals, wherein the distance between each adjacent measuring station of the basic network is between 10 km and 50 km, wherein a subnetwork is subordinated to the base network, wherein subnetwork sensors are distributed in cells of the subnetwork in a smaller distance with a ratio of between 1:8 and 1:12, wherein the sensors located in the basic network, which are in standby-mode and which if receiving Spherics-burst signals in an adjustable time period are self-activating and make a preprocessing for the extraction of event patterns, and wherein the control center turns on said subnetwork sensors for a finer resolution with respect to the observation.

2. The measuring network according to claim 1, wherein the sensors of the base network have three feedback loops, namely, one for self-activating, one for the addition of further bands in the sensor and one for lowering the threshold value in the input circuit of the sensor and wherein the subnetwork sensors do not have feedback loops.

3. The measuring network according to claim 1, wherein the antenna of the sensors of the base network is connected to an input preamplifier, which is connected to a gate circuit for an adjustable threshold value, wherein several digital band filters with 10 kHz to 20 kHz bandwidth are connected to the gate and wherein a part of the band-pass filters serve to the default setting, for processing the frequency components of the signal between zero kHz and 150 kHz, and other digital band filters can be switched on gradually.

4. The measuring network according to claim 1, wherein the sensors of the base network makes a preprocessing of the Spherics-burst signals in such a way, that the received signal after an A/D-conversion are lead over digital band-pass filter working in parallel and the pulse signals located at the ends of the respective frequency bands are in each case analyzed by downstream connected digital signal processors in accordance with frequency of the pulses and power density.

5. The measuring network according to claim 4, wherein a single-chip computer with associated memory unit working as evaluating unit is connected to the digital signal processors for generating an event pattern, and wherein at the output of said evaluating unit for self-activating of the sensor of the base network a modular comparator is arranged, wherein in a first module of said modular comparator (7.8) the event sample at time $T_1$ is stored, wherein in a third module a so-called default pattern is impressed and wherein a second module—in the case of identity of two successive event patterns stored in the first module and the third module—delivers a signal to a power supply unit determined for a transfer unit and activates them.

6. The measuring network according to claim 5, wherein for the addition of further frequency bands and for the variation of the input sensitivity a two-memory comprising a comparator that is connected to the evaluation unit and to a switching unit having a plurality of switches and wherein, if the event patterns stored in the first memory at a time Tn+1 are different from the event patterns stored in the second memory at time Tn, the comparator by means of a switch gradually added on frequency bands by means of a switch or lowers the threshold in a gate circuit to be connected with the antenna.

7. The measuring network according to claim 1, wherein for registration of the real-time signal, the sensors of the basic network have a recording unit, which is designed as a single-chip computer with a corresponding flash memory and is programmable so that the recorded time is to be set manually or can be changed by the control center via the return channel.

8. The measuring network according to claim 1, wherein the subnetwork sensors comprise an input preamplifier connected to an antenna, wherein at output of the preamplifier an A/D converter is connected, wherein at the output of the A/D converter a plurality of parallel-operating digital band-pass filter are connected, the outputs of which for the joint control of a digital signal processor are connected to a multiplexer and a serial connected evaluation unit wherein at the output of the evaluation a transmission device is connected, which in standby operation of the subnetwork sensors is supplied with power by a power supply and wherein by the return channel the power supply for the aforementioned modules can be switched on by the control center.

9. A method for registering weak electromagnetic signals in a measurement system comprising a base network having sensors and a subnet with subnetwork sensors subordinated to the base network according to claim 1, wherein
if receiving Spherics-burst signals incoming in an adjustable time period, the mode sensors of the basic that are in standby-mode are self-activating,
a pre-processing for creating event patterns is performed by the sensors of the basic network and
for finer resolution with respect to the observation the control center turns on the subnetwork sensors.

10. The method according to claim 9, wherein the sensors of based network only be activated and transferring the information to the control center if in said period at least two event patterns are arriving and matching to a given pattern, which is gained by observations through past, and wherein these in the sensors of the based network stored event pattern can be changed remotely if during operation a change of an event pattern selected to flash frequency and/or topography during the initial start-up of the sensors of the basic network sufficiently correlates.

11. The method according to claim 9, wherein the automatic deactivation of sensors of the base network is carried out, if in a predetermined or adjustable period of time any new signals in the respective sensor of the base network is registered.

12. The method according to claim 9, wherein according to the topography for determining the polarization of the source signal and estimating the height position of the sensors of the base network and subnetwork sensors in relation to a source signal instead of an evaluation of the x, y, z-space coordinates only an evaluation in the XY-direction is used.

13. The method according to claim 9, wherein according to the topography not in each cell of the base network the same number of subnetwork sensors is maintained.

14. The method according to claim 9, wherein the method is utilized to make observations in a field of technology selected from a group consisting of agriculture, transport telematics, lightning protection systems, aviation meteorology, earthquake prediction, prediction of volcanic eruptions and medical technology.

* * * * *

UNITED STATES PATENT AND TRADEMARK OFFICE
CERTIFICATE OF CORRECTION

PATENT NO. : 9,488,754 B2
APPLICATION NO. : 14/384525
DATED : November 8, 2016
INVENTOR(S) : Michael J. Pabst It is certified that error appears in the above-identified patent and that said Letters Patent is hereby corrected as shown below:

In the Claims

Column 16, Line 25 (Claim 9, Line 6), insert -- network -- between the words "basic" and "that"

Signed and Sealed this
Tenth Day of January, 2017

Michelle K. Lee
*Director of the United States Patent and Trademark Office*